US010945657B2

(12) United States Patent
Chandrakasan et al.

(10) Patent No.: US 10,945,657 B2
(45) Date of Patent: Mar. 16, 2021

(54) AUTOMATED SURFACE AREA ASSESSMENT FOR DERMATOLOGIC LESIONS

(71) Applicants: Massachusetts Institute of Technology, Cambridge, MA (US); The Brigham and Women's Hospital, Inc., Boston, MA (US)

(72) Inventors: Anantha P. Chandrakasan, Belmont, MA (US); Priyanka Raina, Cambridge, MA (US); Jiarui Huang, Shenzhen (CN); Victor Huang, Sacramento, CA (US)

(73) Assignee: Massachusetts Institute of Technology, Cambridge, MA (US)

( * ) Notice: Subject to any disclaimer, the term of this patent is extended or adjusted under 35 U.S.C. 154(b) by 62 days.

(21) Appl. No.: 15/999,123

(22) Filed: Aug. 17, 2018

(65) Prior Publication Data
US 2019/0053750 A1    Feb. 21, 2019

Related U.S. Application Data

(60) Provisional application No. 62/547,367, filed on Aug. 18, 2017.

(51) Int. Cl.
| | | |
|---|---|---|
| *A61B 5/00* | (2006.01) | |
| *G06T 7/00* | (2017.01) | |
| *G06T 7/11* | (2017.01) | |
| *G06T 7/62* | (2017.01) | |
| *G06T 5/40* | (2006.01) | |

(52) U.S. Cl.
CPC ............ *A61B 5/444* (2013.01); *A61B 5/0077* (2013.01); *G06T 7/0012* (2013.01); *G06T 7/11* (2017.01); *G06T 7/62* (2017.01); *G06T 5/40* (2013.01); *G06T 2207/10004* (2013.01); *G06T 2207/10024* (2013.01); *G06T 2207/10028* (2013.01);
(Continued)

(58) Field of Classification Search
CPC ......... A61B 5/444; A61B 5/0077; G06T 7/62; G06T 7/11; G06T 7/0012
See application file for complete search history.

(56) References Cited

U.S. PATENT DOCUMENTS

| | | |
|---|---|---|
| 5,016,173 A | 5/1991 | Kenet et al. |
| 6,215,893 B1 | 4/2001 | Leshem et al. |

(Continued)

OTHER PUBLICATIONS

Amer et al., "Quality of Life in Patients with Vitiligo: an Analysis of the Dermatology Life Quality Index Outcome Over the Past Two Decades;" International Journal of Dermatology, vol. 55, No. 6; Jun. 2016; pp. 608-614; 7 Pages.
(Continued)

*Primary Examiner* — Md K Talukder
(74) *Attorney, Agent, or Firm* — Daly, Crowley, Mofford & Durkee, LLP

(57) ABSTRACT

A method for assessing a three-dimensional (3D) surface area having one or more lesions is disclosed. The method includes steps of: capturing a two-dimensional (2D) color image and a depth image of the 3D surface area; enhancing contrast of the 2D color image; segmenting the one or more lesions of the 2D color image into one or more segmented lesions; and calculating 3D area of the one or more segmented lesions using information from 2D color image and the depth image.

19 Claims, 8 Drawing Sheets

(52) U.S. Cl.
CPC .............. *G06T 2207/20161* (2013.01); *G06T 2207/30088* (2013.01); *G06T 2207/30096* (2013.01)

(56) References Cited

U.S. PATENT DOCUMENTS

| | | | |
|---|---|---|---|
| 8,755,577 B2 | 6/2014 | Mohamad Hani et al. | |
| 2005/0036668 A1* | 2/2005 | McLennan | G06T 7/0012 382/128 |
| 2007/0195384 A1* | 8/2007 | Lee | G06K 15/1822 358/520 |
| 2010/0185064 A1* | 7/2010 | Bandic | A61B 5/415 600/306 |
| 2010/0266179 A1* | 10/2010 | Ramsay | G06T 7/0012 382/131 |
| 2011/0134312 A1* | 6/2011 | Tay | H04N 5/23293 348/349 |
| 2011/0211754 A1* | 9/2011 | Litvak | G06T 7/73 382/165 |
| 2011/0218428 A1* | 9/2011 | Westmoreland | A61B 6/00 600/425 |
| 2012/0070055 A1* | 3/2012 | Liu | G06T 7/41 382/131 |
| 2012/0183208 A1* | 7/2012 | Sharman | G06T 3/4007 382/162 |
| 2012/0308096 A1* | 12/2012 | Mohamad Hani | A61B 5/444 382/128 |
| 2014/0378810 A1* | 12/2014 | Davis | A61B 5/1034 600/407 |
| 2015/0125092 A1* | 5/2015 | Zhuo | G06T 7/70 382/275 |
| 2015/0286888 A1* | 10/2015 | Maison | G06K 9/3258 382/182 |
| 2015/0374210 A1* | 12/2015 | Durr | A61B 1/07 600/111 |
| 2016/0104031 A1* | 4/2016 | Shotton | G06K 9/00201 382/154 |
| 2016/0171695 A1* | 6/2016 | Jacobs | G06T 11/005 382/131 |
| 2017/0124709 A1 | 5/2017 | Rithe et al. | |
| 2018/0047175 A1* | 2/2018 | Wang | G06T 7/11 |
| 2018/0240238 A1* | 8/2018 | Husheer | G06K 9/00362 |
| 2018/0374203 A1* | 12/2018 | Xiao | G06T 5/009 |
| 2019/0053750 A1* | 2/2019 | Chandrakasan | G06T 7/0012 |
| 2019/0298252 A1* | 10/2019 | Patwardhan | A61B 5/0082 |
| 2020/0104034 A1* | 4/2020 | Lee | H04N 5/2258 |

OTHER PUBLICATIONS

Ferreira et al., "ImageJ User Guide;" Revised Edition IJ 1.46r; Retrieved from http://imagej.nih.gov/ij/docs/guide; Oct. 2, 2012; 198 Pages.

Komen et al., "Vitiligo Area Scoring Index and Vitiligo European Task Force Assessment: Reliable and Responsive Instruments to Measure the Degree of Depigmentation in Vitiligo;" British Journal of Dermatology (BJD), vol. 172, No. 2; Oct. 3, 2014; pp. 437-443; 7 Pages.

Smith&Nephew, "Visitrak Digital Instruction Manual;" Retrieved from https://www.smith-nephew.com/global/assets/pdf/products/surgical/2-visitrakdigitaluserguide.pdf on Nov. 9, 2018; 8 Pages.

Yang et al., "Color-Guided Depth Recovery from RGB-D Data Using an Adaptive Autoregressive Model;" IEEE Transactions on Image Processing, vol. 23, No. 8; Aug. 2014; pp. 3443-3458; 16 Pages.

Zuiderveld, "Contrast Limited Adaptive Histogram Equalization;" Chapter VIII.5 from *Graphis Gems IV*; Academic Press Professional, Inc.; Jan. 1994; pp. 474-485; 12 Pages.

Achanta et al., "SLIC Superpixels Compared to State-of-the-art Superpixel Methods;" Journal of Latex Class Files, vol. 6, No. 1; Dec. 2011; 8 Pages.

Al-Ameen et al., "An Innovative Technique for Contract Enhancement of Computer Tomography Images Using Normalized Gamma-Corrected Contrast-Limited Adaptive Histogram Equalization;" EURASIP Journal on Advances in Signal Processing; Apr. 1, 2015; 12 Pages.

Bansal et al., "Color Image Segmentation Using CIELab Color Space Using Ant Colony Optimization;" International Journal of Computer Science & Engineering Technology, vol. 1, Issue 7; Aug. 2011; 6 Pages.

Beucher, "The Watershed Transformation Applied to Image Segmentation;" in Scanning Microscopy International; Jul. 2000; 26 Pages.

Chang et al., "A Comparison of Wound Area Measurement Techniques: Visitrak Versus Photography;" Open Access Journal of Plastic Surgery (Eplasty); Published Apr. 18, 2011; 10 Pages.

Gonzalez et al., "*Digital Image Processing*;" Third Edition; Pearson Education, Inc.; Jan. 1, 2008; 122 Pages.

Hayashi et al., "A Novel Three Dimensional Imaging Method for the Measurement of Area in Vitiligo and Chemical Leukoderma;" Letters to the Editor in Journal of Dermatological Science, vol. 84; Aug. 22, 2016; 3 Pages.

Khoo et al., "The Evolving Field of Wound Measurement Techniques: A Literature Review;" Wounds, vol. 28, No. 6; Jun. 2016; 7 Pages.

Kohli et al., "Three-Dimensional Imaging of Vitiligo;" Experimental Dermatology—Methods Letter to the Editor in Experimental Dermatology, vol. 24, No. 11; Jun. 2015; 2 Pages.

Le et al., "Directional Joint Bilateral Filter for Depth Images;" Article in Sensors Journal, vol. 14, No. 7; Jun. 2014; 17 Pages.

Lee et al., "A Flexible Architecture for Precise Gamma Correction;" IEEE Transactions on Very Large Scale Integration (VLSI) Systems, vol. 15, No. 4; Apr. 2007; 5 Pages.

Lowe, "Object Recognition from Local Scale-Invariant Features;" Proceedings of the Seventh IEEE International Conference on Computer Vision, vol. 2; Sep. 1999; 8 Pages.

Neverova et al., "2½D Scene Reconstruction of Indoor Scenes from Single RGB-D Images;" International Workshop on Computational Color Imaging (CCIW); Mar. 3, 2013; 15 Pages.

Pizer et al., "Adaptive Histogram Equalization and its Variations;" Computer Vision, Graphics, and Image Processing, vol. 39, Issue 3; Sep. 1987; 14 Pages.

Rithe, "Energy-Efficient System Design for Mobile Processing Platforms;" Dissertation of Massachusetts Institute of Technology; Jun. 2014; 100 Pages (Part 1 of 2).

Rithe, "Energy-Efficient System Design for Mobile Processing Platforms;" Dissertation of Massachusetts Institute of Technology; Jun. 2014; 103 Pages (Part 2 of 2).

Roerdink et al., "The Watershed Transform: Definitions, Algorithms and Parallelization Strategies;" Fundamenta Informaticae 41; IOS Press; Jan. 2001; 40 Pages.

Rother et al., ""GrabCut"—Interactive Foreground Extraction Using Iterated Graph Cuts;" Journal of ACM Transactions on Graphics (SIGGRAPH); Aug. 1, 2004; 6 Pages.

Salzes et al., "The Vitiligo Impact Patient Scale (VIPs): Development and Validation of a Vitiligo Burden Assessment Tool;" Journal of Investigative Dermatology, vol. 136; Jan. 2016; 7 Pages.

Schneider et al., "NIH Image to ImageJ: 25 Years of Image Analysis;" Nature Methods, vol. 9, No. 7; Jul. 2012; 5 Pages.

Shamsudin et al., "Objective Assessment of Vitiligo with a Computerised Digital Imaging Analysis System;" Australasian Journal of Dermatology, vol. 56, No. 4; Dec. 2014; 5 Pages.

Shen et al., "Layer Depth Denoising and Completion for Structured-Light RGB-D Cameras;" Proceedings of the 2013 IEEE Conference on Computer Vision and Pattern Recognition (CVPR); Jun. 23, 2013; 8 Pages.

Sheth et al., "A Pilot Study to Determine Vitiligo Target Size Using a Computer-Based Image Analysis Program;" Journal of the American Academy of Dermatology; Aug. 2015; 4 Pages.

Shetty et al., "A Novel and Accurate Technique of Photographic Wound Measurement;" Indian Journal of Plastic Surgery, vol. 45, Issue 2; May-Aug. 2012; 5 Pages.

Smith & Nephew, "Visitrak Digital Instruction Manual;" Jan. 2003; www.smith-nephew.com; 8 Pages.

(56) References Cited

OTHER PUBLICATIONS

Song et al., "Depth Completion for Kinect v2 Sensor;" Multimedia Tools and Applications, vol. 76, Issue 3; Feb. 2017; 24 Pages.
Tay et al., "Pilot Study of an Automated Method to Determine Melasma Area and Severity Index;" British Journal of Dermatology (BJD), vol. 172; Jan. 20, 2015; 6 Pages.
Van Geel et al., "A New Digital Image Analysis System Useful for Surface Assessment of Vitiligo Lesions in Transplantation Studies;" European Journal of Dermatology (EJD), vol. 14, No. 3; May 2004; 6 Pages.
Wikipedia, "File:Surface integral1.svg;" Retrieved from https://en.wikipedia.org/wiki/File:Surface_integral1.svg; 4 Pages.
Wikipedia, "Kinect;" Retrieved from https://en.wikipedia.org/wiki/Kinect; 21 Pages.
Zhang, "A Flexible New Technique for Camera Calibration;" IEEE Transactions on Pattern Analysis and Machine Intelligence, vol. 22, No. 11; Nov. 2000; 5 Pages.
Zhang et al., "A Fast 3D Reconstruction System with a Low-Cost Camera Accessory;" Scientific Reports, No. 5; Published Jun. 9, 2015; 7 Pages.

\* cited by examiner

AUTOMATED SURFACE AREA ASSESSMENT FOR DERMATOLOGIC LESIONS

CROSS-REFERENCE TO RELATED APPLICATIONS

This application claims the benefit of Provisional Application No. 62/547,367 filed Aug. 18, 2017, and entitled "AUTOMATED SURFACE AREA ASSESSMENT FOR DERMATOLOGIC LESIONS," which application is hereby incorporated herein by reference in its entirety.

TECHNICAL FIELD

This disclosure generally relates to a method for assessing a surface area of lesions and more particularly to a method for assessing a surface area of dermatologic lesions using a two-dimensional color image and a corresponding depth image.

BACKGROUND

For a dermatologic disease that is related to skin, nails, or hair, it is important to assess the extent and severity of the disease properly. The severity of the disease is commonly measured by assessing the body surface area (BSA) covered by lesions resulting from the disease or the volume of cutaneous wounds. Correct initial assessment of BSA or wound volume is critical, both to the initial assessment of a disease severity as well as to the evaluation of disease progression or improvement. The most common method of assessment in clinical practice is based on a physician's visual estimation of area involvement, which has low accuracy and reproducibility.

Moreover, these assessments often have been performed by non-dermatologists with no training to complete such assessments. This limitation represents a major hurdle for clinical trials, translational research efforts, as well as daily clinical care. For example, estimation of BSA helps determine who is a candidate for systemic immuno-suppression for psoriasis and atopic dermatitis among other diseases. Correct assessment of lesions also is a key factor in determining a grade of cutaneous adverse reactions to chemo- and immuno-therapies and determines whether a patient can stay on cancer therapy. Response to treatment for chronic wounds is also dependent on crude estimations of wound volume.

The most widely used method for assessing BSA in clinics is visual observation, which is subjective and, therefore, has low accuracy and reproducibility. A more accurate system called Visitrak™ is available, where a lesion is manually traced onto a transparent grid sheet, which is then retraced onto the Visitrak™ pad that automatically completes the area calculations. The Visitrak™ system, however, is prohibitively time-consuming because of the associated manual tracing of lesions and the subsequent retracing of lesions on the Visitrak™ pad required for area determination.

Image analysis programs which perform automatic lesion segmentation from 2D color images of a lesion have also been developed. One such program is the so-called ImageJ program. Such programs, however, only provide the relative change in lesion area from a sequence of images. Such programs do not provide an absolute measurement of the lesions (i.e. a measurement corresponding to a specific area measurement, e.g. expressed in units such as centimeters squared), which makes comparing different lesions for the same person or across different people extremely difficult if not impossible. The image analysis program also fails at assessing large lesions and gives inaccurate measurement over curved surfaces.

In addition, there are other methods developed to analyze images of the lesions to assess the surface area. However, those methods often produce the inaccurate measurement because the methods do not consider that the surface area is curved. Calculation of the area with a projected surface area introduces up to 50% error depending on the angle at which the 2D image is captured.

Accordingly, a new system that addresses these shortcomings of the previous methods is needed.

SUMMARY

In this work, systems and techniques have been developed that provide rapid, reproducible and objective determination of BSA. The proposed solution to this problem is the development of a 3D imaging platform that is computationally efficient and requires minimal resources to implement. The image acquisition is based on available ambient light sources enhanced by supplementary lighting (e.g., Wood's lamp or flashes used in standard and UV photography), so as to be attainable with minimal specialized equipment. The processing is largely automated enabling lesion segmentation and area determination without the need to manually determine lesion boundaries.

One aspect of the concepts described herein is the development of a tool and associated image processing/enhancement algorithms to enable the rapid, reproducible, and objective determination of the surface area in an automated fashion via 3D imaging. According to one illustrative embodiment, a method for assessing a three-dimensional (3D) surface area having one or more lesions may include the unordered steps of: capturing a two-dimensional (2D) color image and a depth image of the 3D surface area; enhancing contrast of the 2D color image; segmenting the one or more lesions of the 2D color image into one or more segmented lesions; and calculating 3D area of the one or more segmented lesions using information from 2D color image and the depth image.

In one variation of the illustrative embodiment, the method may include calibrating at least one parameter for processing the depth image.

In one variation of the illustrative embodiment, the method may include mapping pixels of the 2D color image to depth pixel of the depth image.

In one variation of the illustrative embodiment, the step of enhancing contrast of the 2D color image may include applying gamma correction to each of color channels of the 2D color image.

In one variation of the illustrative embodiment, the step of enhancing contrast of the 2D color image may include applying histogram equalization to the 2D color image.

In one variation of the illustrative embodiment, the step of enhancing contrast of the 2D color image may include: dividing the 2D color image into a plurality of tiled images; applying the histogram equalization method to each of the tiled images; and combining the plurality of images into a combined two-image. Herein, the step of enhancing contrast of the 2D color image may include softening borders of each of the tiled images by applying the bilinear interpolation method.

In one variation of the illustrative embodiment, the method may include converting an RGB color space of the 2D color image into a Lab color space; adjusting a lightness channel of the 2D color image; and converting the color space of the 2D color image to the RGB color space.

In one variation of the illustrative embodiment, the step of segmenting the surface area may include segmenting the one or more lesions of the 2D color image into one or more segmented lesions using the watershed transformation.

In one variation of the illustrative embodiment, the step of calculating 3D area of the one or more lesions may include: calculating depth values for each pixel of the depth image; and calculating the 3D area of one or more lesions considering the depth values. Herein, the step of calculating 3D area of the one or more lesions may include calculating the 3D area of one or more lesions considering the gradient of the depth values.

In one variation of the illustrative embodiment, the method may include approximating the gradient of the depth values using a central difference of horizontally aligned pixels and vertically aligned pixels in the depth image.

In one variation of the illustrative embodiment, the method may include calculating the 3D area of one or more lesions using the following formulas:

$$\text{Lesion area} \cong \sum_{(i,j) \in \text{Lesion}} D(i, j)^2 \sqrt{D_x(i, j)^2 + D_y(i, j)^2 + 1} \theta_x \theta_y$$

$$D_x(i, j) = \frac{D(i+1, j) - D(i-1, j)}{2D(i, j)\theta_x}, \quad D_y(i, j) = \frac{D(i, j+1) - D(i, j-1)}{2D(i, j)\theta_y}$$

where (i, j) are pixel coordinates, D(i, j) is the depth of pixel (i, j), and the camera has a field of view Fx×Fy degrees with a resolution of Rx×Ry pixels and each image pixel corresponds to a field of view of θx×θy degrees where θx=Fx/Rx and θy=Fy/Ry.

In one variation of the illustrative embodiment, the method may include measuring distance to each of pixels of the depth image by measuring the time of flight between the each of pixels and a camera capturing the depth image.

According to another illustrative embodiment, an apparatus for assessing a three-dimensional (3D) surface area having one or more lesions, the apparatus may include a camera capturing a two-dimensional (2D) color image and a depth image of the 3D surface area; and a processor and a memory, wherein the processor is configured to: enhance contrast of the 2D color image; segment the one or more lesions of the 2D color image into one or more segmented lesions; and calculate 3D area of the one or more segmented lesions using information from 2D color image and the depth image.

In one variation of the illustrative embodiment, the camera may measure distance to each of pixels of the depth image by measuring the time of flight between the each of pixels and the camera.

In one variation of the illustrative embodiment, the apparatus may include a user interface with which a user enhances the contrast of the 2D color image. Herein, the user may select a type of histogram equalization to enhance the contrast of the 2D color image via the user interface.

The details of one or more embodiments of the disclosure are outlined in the accompanying drawings and the description below. Other features, objects, and advantages of the disclosure will be apparent from the description and drawings, and from the claims.

BRIEF DESCRIPTION OF THE DRAWINGS

The foregoing features may be more fully understood from the following description of the drawings in which.

DETAILED DESCRIPTION

Figure 1:
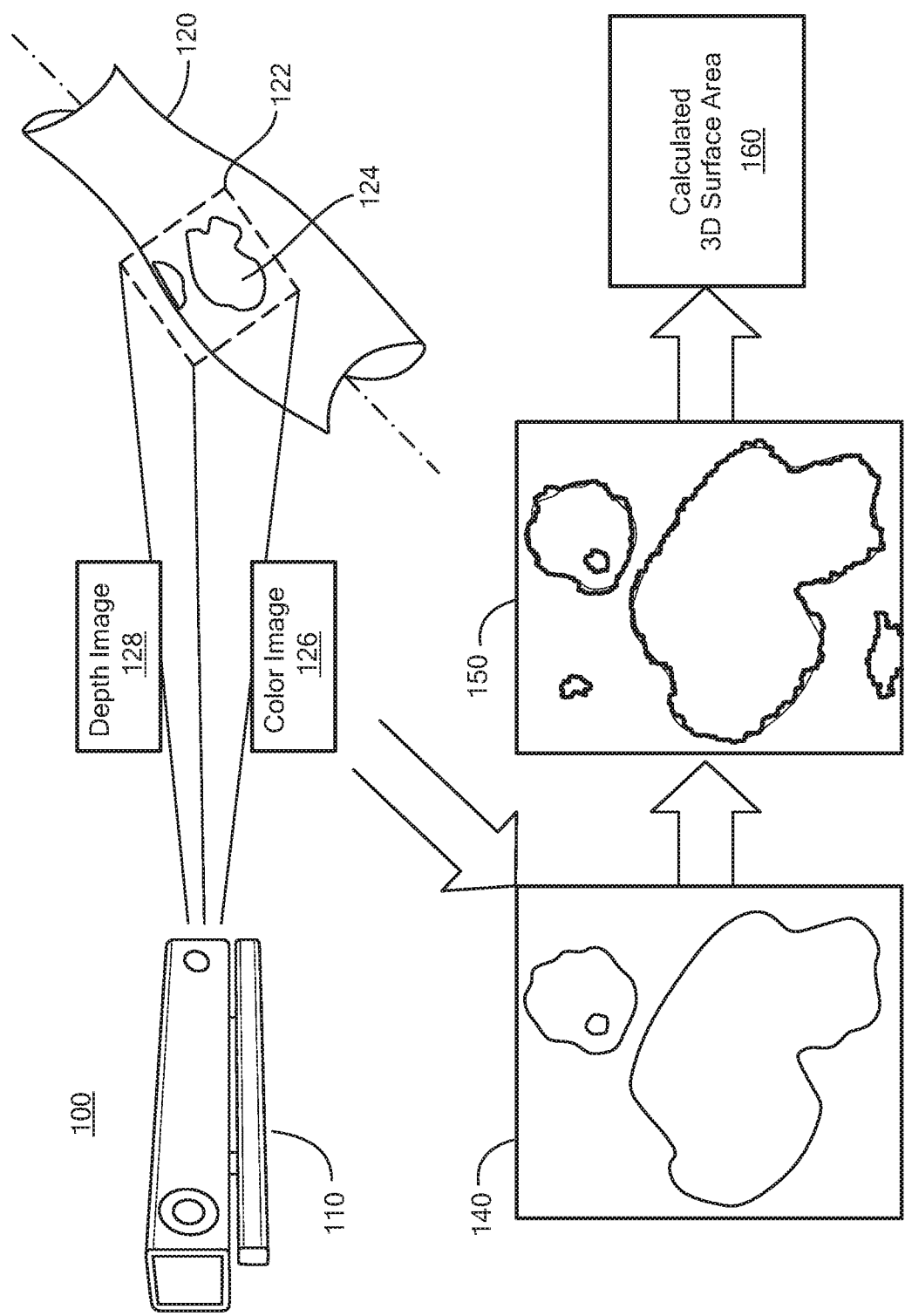
FIG. 1 is an illustrative system for processing images of a lesion to determine a three-dimensional (3D) surface area of the lesion according to the concepts described herein.

All relative descriptions herein, such as left, right, up, and down, are with reference to the figures, and not meant in a limiting sense. Additionally, for clarity, common items and circuitry, such as integrated circuits, resistors, capacitors, transistors, and the like, have not been included in the figures, as can be appreciated by those of ordinary skill in the pertinent art. Unless otherwise specified, the illustrated embodiments may be understood as providing example features of varying detail of certain embodiments, and therefore, unless otherwise specified, features, components, modules, elements, and/or aspects of the illustrations can be otherwise combined, interconnected, sequenced, separated, interchanged, positioned, and/or rearranged without materially departing from the disclosed concepts, systems, or methods. Additionally, the shapes and sizes of components are intended to be only illustrative and unless otherwise specified, can be altered without materially affecting or limiting the scope of the concepts sought to be protected herein.

Before describing an automated surface area assessment system suitable for detection and assessment of lesions wounds and the like which may exist on a body, and the operations performed to determine a three-dimensional (3D) surface area, some introductory concepts and terminology are explained.

An analog or continuous parameter image such as a still photograph may be represented as a matrix of digital values and stored in a storage device of a computer or other digital processing device. Thus, as described herein, the matrix of digital data values are generally referred to as a "digital image" or more simply an "image" and may be stored in a digital data storage device, such as a memory for example, as an array of numbers representing the spatial distribution of energy at different wavelengths in the image.

Similarly, an image sequence such as a view of a moving roller-coaster for example, may be converted to a digital video signal as is generally known. The digital video signal is provided from a sequence of discrete digital images or frames. Each frame may be represented as a matrix of digital data values which may be stored in a storage device of a computer or other digital processing device. Thus, in the case of video signals, as described herein, a matrix of digital data values is generally referred to as an "image frame" or more simply an "image" or a "frame." Each of the images in the digital video signal may be stored in a digital data storage device, such as a memory for example, as an array of numbers representing the spatial distribution of energy at different wavelengths in a scene in a manner similar to the manner in which an image of a still photograph is stored.

Whether provided from a still photograph or a video sequence, each of the numbers in the array correspond to a digital word (e.g. an eight-bit binary value) typically referred to as a "picture element" or a "pixel" or as "image data." The image may be divided into a two-dimensional array of pixels with each of the pixels represented by a digital word.

Reference is sometimes made herein to color images with only a luminance component. Such images are known as gray scale images. Thus, a pixel represents a single sample which is located at specific spatial coordinates in the image. It should be noted that the techniques described herein may be applied equally well to either grey scale images or color images.

In the case of a gray scale image, the value of each digital word corresponds to the intensity of the pixel and thus the image at that particular pixel location.

In the case of a color image, reference is sometimes made herein to each pixel being represented by a predetermined number of bits (e.g. eight bits) which represent the color red (R bits), a predetermined number of bits (e.g. eight bits) which represent the color green (G bits) and a predetermined number of bits (e.g. eight bits) which represent the color blue (B-bits) using the so-called red-green-blue (RGB) color scheme in which a color and luminance value for each pixel can be computed from the RGB values. Thus, in an eight bit color RGB representation, a pixel may be represented by a twenty-four bit digital word.

It is of course possible to use greater or fewer than eight bits for each of the RGB values. It is also possible to represent color pixels using other color schemes such as a hue, saturation, brightness (HSB) scheme or a cyan, magenta, yellow, black (CMYK) scheme. It should thus be noted that the techniques described herein are applicable to a plurality of color schemes including but not limited to the above mentioned RGB, HSB, CMYK schemes as well as the Luminosity and color axes a & b (Lab), YUV color difference color coordinate system, the Karhunen-Loeve color coordinate system, the retinal cone color coordinate system and the X, Y, Z scheme.

Reference may also sometimes be made herein to an image as a two-dimensional pixel array. An image may be represented, for example, as a pixel array having a number of rows and a number of columns. An example of an array size is size 512 rows and 512 columns (demoted as a 512×512 array). One of ordinary skill in the art will recognize, of course, that the techniques described herein are applicable to various sizes and shapes of pixel arrays including irregularly shaped pixel arrays.

The processing described herein may take place on only a portion of an image. For example, if an image is provided as a 512×512 pixel array, a portion of the image on which processing may be applied may correspond to a 32×32 portion of the 512×512 pixel array.

Referring now to FIG. 1, an illustrative diagram showing an automated surface area assessment system 100 is presented according to the concepts described herein. The system 100 may comprise two parts. The first part may be capturing an image of a surface area 120 and the second part may be processing the image to calculate a 3D surface area of lesions in the image. The surface area 120 may have one or more lesions affected by a dermatologic disease. As shown in the illustrative example, the surface area is a three-dimensional object having a curved surface, such as a limb or a food of human body. For example, vitiligo is a long-term skin condition characterized by patches of skin losing their pigment. The patches of affected skin become white and usually have sharp margins. Vitiligo affects people with all skin types but is most noticeable in those with dark skin. An exemplary implementation of the automated surface area assessment system 100 may be implemented to assess lesions from vitiligo. However, as can be appreciated by those of ordinary skill in the pertinent art, the system 100 may be used to assess lesions from any other diseases including but not limited to psoriasis, melanoma, wounds, as well as lesions resulting from dermatologic reactions to drugs Herein, an image acquisition system 110 (e.g. a camera or any other type of imaging device) may capture a color image of the surface area 122 having one or more lesions 124. The image acquisition system 110 stores a color image 126 of the surface area 120. The color image 126 may be a two-dimensional color image that contains a plurality of pixels having information of corresponding points of the surface area 120. The color image 126 may be stored in any type of format including, but not limited to a .jpg format or a .png format, as a picture 140 that contains a projected image of the target surface area 122. In an illustrative embodiment, the color image 126 may be stored as an RGB image. An RGB image is an ordinary image with a vector of three values stored in each pixel. These three values represent the intensity of each color. For example, a pixel with a color tuple of [255, 0, 0] is red and a pixel with a color tuple of [0, 0, 0] is black. Alternately, as can be appreciated by those of ordinary skill in the pertinent art, the color image 126 may be stored in any suitable format.

The camera 110 may also capture a depth image 128 of the surface area. A depth image is an image in which each pixel also has associated therewith a distance to a corresponding point on the surface 120 being imaged.

In an illustrative embodiment, the camera may be a Microsoft Kinect. Kinect is a motion sensing input device by Microsoft for Xbox 360, Xbox One video game consoles and Microsoft Windows PCs. Kinect has built-in color and infrared cameras, which enable a user to capture depth and color images at the same time. There are two versions of Kinect—Kinect V1 and Kinect V2. The major differences between these two generations of Kinects are image resolutions and sensing techniques. Kinect V1 has a color image resolution of 640×480 pixels and a depth image resolution of 320×240 pixels while Kinect V2 has a color image resolution of 1920×1080 pixels and a depth image resolution of 512×424 pixels. In order to capture depth to the target object, Kinect V1 uses stereopsis while Kinect V2 uses time-of-flight for depth measurement. The time of flight (TOF) is the time that an object needs to travel a distance through a medium. The measurement of this time (i.e. the time of flight) can be used for measuring a velocity of the object or a distance to the target area. Because of the different techniques used between Kinect V1 and Kinect V2 to measure depth, the effective depth measurement ranges are also different. However, as can be appreciated by those of ordinary skill in the pertinent art, other technologies that are able to capture a color image and a depth image of a surface area may be used.

Once the 2D color image 126 and the depth image 128 are captured, the system 100 may store the image files into a storage unit (not shown). The system 100 may parse the 2D color image 126 and the depth image 128 and store corresponding data into a different format, which is more convenient for later use. In some embodiments, the system may store both the original image files and parsed data files.

In some embodiments, the image acquisition system may automatically produce a depth image having which is associated (or "mapped to") corresponding pixels of a 2D color image.

In embodiments in which the color image and the depth image are captured by different systems, in order to calculate the 3D surface area, it is necessary to "map" (or associate) the depth image data 128 to the appropriate 2D color image data 126. However, the color image and the depth image may be captured by different methods and as a result may have different resolutions. Simply scaling them and stacking one image on top of the other image may not give desirable results. For this reason, a coordinate mapping unit (614 in FIG. 6) may map each color pixel of the color image 126 to corresponding depth pixel in the depth image 128 in order to obtain depth information.

In some embodiments, the camera 110 may embed a coordinate mapping unit to produce a color image, a depth image, and mapping data. Alternately, the coordinate mapping can be performed by other elements of the system 100. In some embodiments, if a pixel in the RGB image is not mapped to any pixel in the depth image, then the corresponding pixel in the mapped depth image is completely black, meaning that the pixel in the color image does not have a mapped depth pixel. This situation may happen when the color image and the depth image have different resolutions. In this situation, the system may set depth values of the pixels that do not have corresponding depth data with an average depth of their adjacent pixels.

The system 100 may align the 2D color image 126 with the depth image 128. In some embodiments, an image alignment unit (632 in FIG. 6) may align the images. The alignment may be trivial when the color image and the depth image are mapped by the coordinate mapping unit. After that, the system 100 may enhance the contrast of the 2D color image 126. For example, regarding to vitiligo disease, skin de-pigmentation is visually different on various types of skin. Vitiligo lesions on the lighter skin may be less distinguishable than those on darker skin. The system, therefore, incorporates a contrast enhancement tool to aid lesion segmentation that will be explained in detail in the process 300 in FIG. 3. After the color image enhancement, the 2D color image is enhanced to show the lesions more clearly as in 150.

The system 100 may segment lesions of the surface area in the enhanced color image 150. In some embodiments, the system may use the watershed algorithm to perform the segmentation. Alternately, the system may use the grabcut segmentation method. In other embodiments, the system may use any other suitable methods to segment the lesions. After lesion segmentation, the system 100 may calculate the lesion area. The procedure to calculate the lesion area will be explained in detail in the process 400 of FIG. 4. Once the calculation of the lesion area, the system may provide the calculated 3D surface area 160 to a user.

FIGS. 2-5 are a series of flow diagrams illustrating the processing performed by the apparatus to produce a 3D surface area or a lesion. The rectangular elements (typified by element 210), herein denoted "processing blocks," represent computer software instructions or groups of instructions. The diamond shaped elements (typified by element 320), herein denoted "decision blocks," represent computer software instructions, or groups of instructions which affect the execution of the computer software instructions represented by the processing blocks. The flow diagram does not depict syntax of any particular programming language. Rather, the flow diagram illustrates the functional information one skilled in the art requires to generate computer software to perform the processing required of system 100 (and/or system 600). It should be noted that many routine program elements, such as initialization of loops and variables and the use of temporary variables are not shown. Further, the processing and decision blocks are unordered meaning that the processing performed in the blocks can done in any convenient or desirable order unless otherwise stated or an order is evident from the context.

Figure 2:
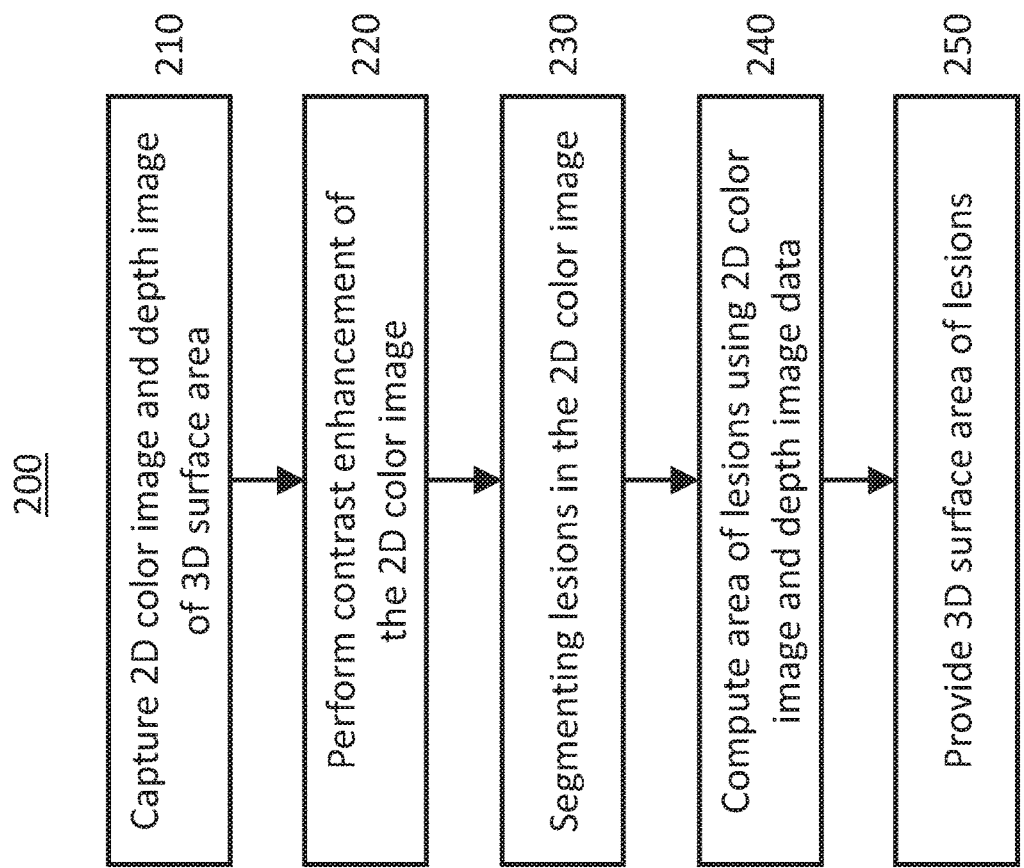
FIG. 2 is a flowchart of an automated surface area assessment technique according to the concepts described herein.

Referring now to FIG. 2, a flowchart 200 for assessing a three-dimensional (3D) surface area is presented according to the concepts described herein. In processing block 210, a camera or other image acquisition system (which may be the same as or similar to image acquisition system 110 described above in conjunction with FIG. 1) may capture a color image (which may be the same as or similar to color image 126 described above in conjunction with FIG. 1) and a depth image of a surface area (e.g. surface area 120 described above in conjunction with FIG. 1). In processing block 220, the contrast of the color image (e.g. color image 126 in FIG. 1) is enhanced. Such enhancement may be accomplished, for example, using the process described below in conjunction with FIG. 3.

In processing block 230, lesions in the enhanced color image are segmented. Such segmentation may be accomplished, for example, using any segmentation technique known to those of ordinary skill in the art as long as the segmentation may be accomplished at a sufficiently fine level of segmentation such that a trace of the lesion boundary (i.e. a border which defines the edge of a lesion) may be formed. This is in contrast to prior art approaches in which a box is drawn around the lesion rather than a trace of the lesion boundary). For example, a so-called grabcut technique or a so-called watershed technique may be used to segment the color image. The grabcut technique is an image segmentation method based on graph cuts. The algorithm can be described as follows: 1) User specifies a rectangle box that bounds the object. Everything outside is taken as sure background; 2) Algorithm initializes labelling of the foreground and background pixels. The user can also correct background and foreground labelling manually; 3) A Gaussian Mixture Model (GMM) is used to model the foreground and background; 4) A graph is built from this pixel distribution. In the graph, the pixels are nodes and weights of edges connecting two nodes depend on pixel similarity; 5) A min-cut algorithm is performed to segment the graph into foreground and background. The steps 3)-5) may be repeated as required.

Alternately, the watershed technique may be applied to address a limitation of grabcut technique, which does not perform as expected on objects that are not bounded or on multiple objects. The watershed technique is a transformation that relies on a geological watershed, or drainage divide, which separates adjacent drainage basins. The watershed transformation may treat the image as like a topographic map, with the brightness of each point representing its height, and finds the lines that run along the tops of ridges.

There are various options for how to apply the watershed transformation to segment an image. In some embodiments, the watershed technique may allow the user to select background and foreground so that the image can be more accurately segmented.

Then, the system determines the 3D surface area of each lesion using information from the 2D color image and the depth image in processing block 240. In processing block 250, the system provides the 3D surface area of the lesions. Now, each of the processing blocks 220 and 240 will be explained in detail in the following processes.

Figure 3:
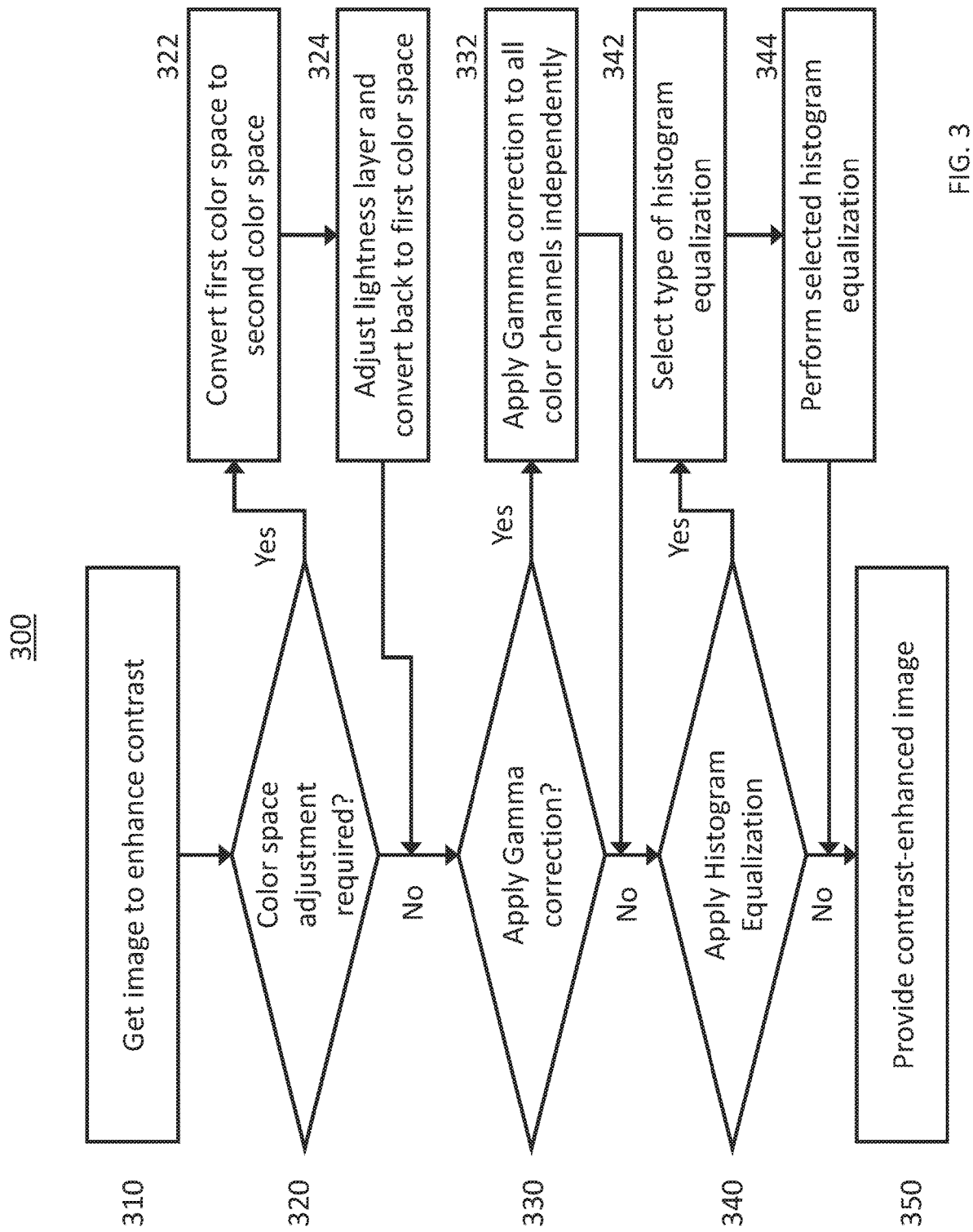
FIG. 3 is a flowchart of a process for enhancing the contrast of a two-dimensional (2D) color image according to the concepts described herein.

Referring now to FIG. 3, a flowchart 300 for enhancing the contrast of a two-dimensional (2D) color image is presented according to the concepts described herein. For some lesions of surface area, it may be difficult to determine the boundary of the lesions. For example, de-pigmentation from vitiligo disease is visually different on various types of skin. Vitiligo lesions on the lighter skin may be less distinguishable than those on darker skin. Accordingly, contrast enhancement of the image may be necessary before calculating the area of the lesions.

In processing block 310, the system (e.g. via contrast enhance unit 612 discussed in FIG. 6) receives a 2D color image to enhance the contrast of the image. If needed, the 2D color image may be aligned with a respective depth image. In processing block 320, the system may determine whether a color space adjustment is required. If it is determined to adjust the color space of the image, processing proceeds to processing block 322 in which the data as measured in a first color space (e.g. one of the aforementioned RGB, HSB, CMYK, Lab schemes or the YUV color difference color coordinate system, the Karhunen-Loeve color coordinate system, the retinal cone color coordinate system and the X, Y, Z scheme is converted to a second, different color space (e.g. a different one of the aforementioned RGB, HSB, CMYK, Lab schemes or the YUV color difference color coordinate system, the Karhunen-Loeve color coordinate system, the retinal cone color coordinate system and the X, Y, Z scheme).

For example, in a system in which an image acquisition system produces a color image in the RGB color space, the system may convert the RGB space to a Lab color space in processing block 322. Lab color space is designed to approximate human vision. The lab color space describes perceivable colors using three parameters: L for lightness, a for green-red color opponents and b for blue-yellow color opponents. By converting the original image from RGB color space to Lab color space, this system can adjust the lightness layer to reveal hidden details that are not apparent, without losing the color features. After the adjustment, the color image may be converted back from the lab color space into an RGB image for further processing (processing block 324). In some embodiments, this system may provide a user interface with which a user may select an option to perform color adjustment in Lab color space. Herein, the user interface may provide addition option to the user to select other image enhancement options described below.

In processing block 330, the system (e.g. contrast enhancement unit 632) may determine whether a gamma correction needs to be applied to the color image. In some embodiments, the user may select to apply gamma correction with the user interface described above. Gamma correction, or gamma transformation, is a nonlinear operation used to encode and decode luminance or tristimulus values in an image. Usually, Gamma correction controls the overall brightness of an image. Images that are not properly corrected can look either too bright or too dark. Varying the amount of gamma correction changes not only the brightness, but also the ratios of red to green to blue. If it is determined to apply gamma correction in processing block 330, the system may apply gamma correction to each color channels of the color image in step 332. For an input pixel I(x, y) and its corresponding output pixel O(x, y), the gamma correction is applied as follows:

$$O(x, y) = [\alpha * I(x, y) + \beta]^{\frac{1}{\gamma}}$$

where α operates as an intensity amplifier, β a range shift, and γ the gamma coefficient. The difference in intensity between two pixels will be accentuated if γ<1 and lessened if γ>1. The original image is returned when γ=1. This transformation in intensity may involve only three parameters. Herein, the gamma correction may be applied to all three-color channels independently.

In processing block 340, the system (e.g. contrast enhancement unit 632) determines whether histogram equalization is needed. In some embodiments, the user may select to apply histogram equalization with the user interface described above. If it is determined to apply histogram equalization, the system may determine a type of histogram equalization to apply to the color image in processing block 332. Herein, the system may apply a standard histogram equalization or an adaptive histogram equalization. The system may apply the selected histogram equalization to the image in processing block 334.

The standard histogram equalization is a technique for adjusting image intensities to enhance contrast. A histogram is a graphical representation of the pixel intensities in the image. The left side of the graph represents the information in the darker areas in the image and the right side represents the brighter area. The height of each bar indicates the frequency of pixels in a specific intensity range, typically from 0 to 255. Herein the histogram equalization is explained for a grayscale input image X with gray levels ranging from 0 to L−1. From a probabilistic model point of view, each bar in the histogram of this image represents the probability density of pixels with gray level i. In this case, a cumulative distribution function $F_X(i)$ of pixels with intensity level i is defined as:

$$F_X(i) = \sum_{j=0}^{i} \frac{n_j}{n}$$

where nj is the number of pixels with gray level j and n the total number of pixels in the image. Histogram equalization may convert an input image to the output image Y such that $F_Y(i)$ is linear, meaning that the most frequent intensity values in the image are spread out and therefore increases the global contrast of the image.

Alternately, an adaptive histogram equalization may be selected. The standard histogram equalization considers the global contrast of the image. However, in many cases, it is sub-optimal. An improved technique known as an adaptive histogram equalization is used to provide better contrast processing. In the illustrative embodiment in FIG. 3, the color space adjustment, gamma correction and histogram equalization are performed in the order. However, those contrast enhancement methods may be executed in any order.

Figure 4:
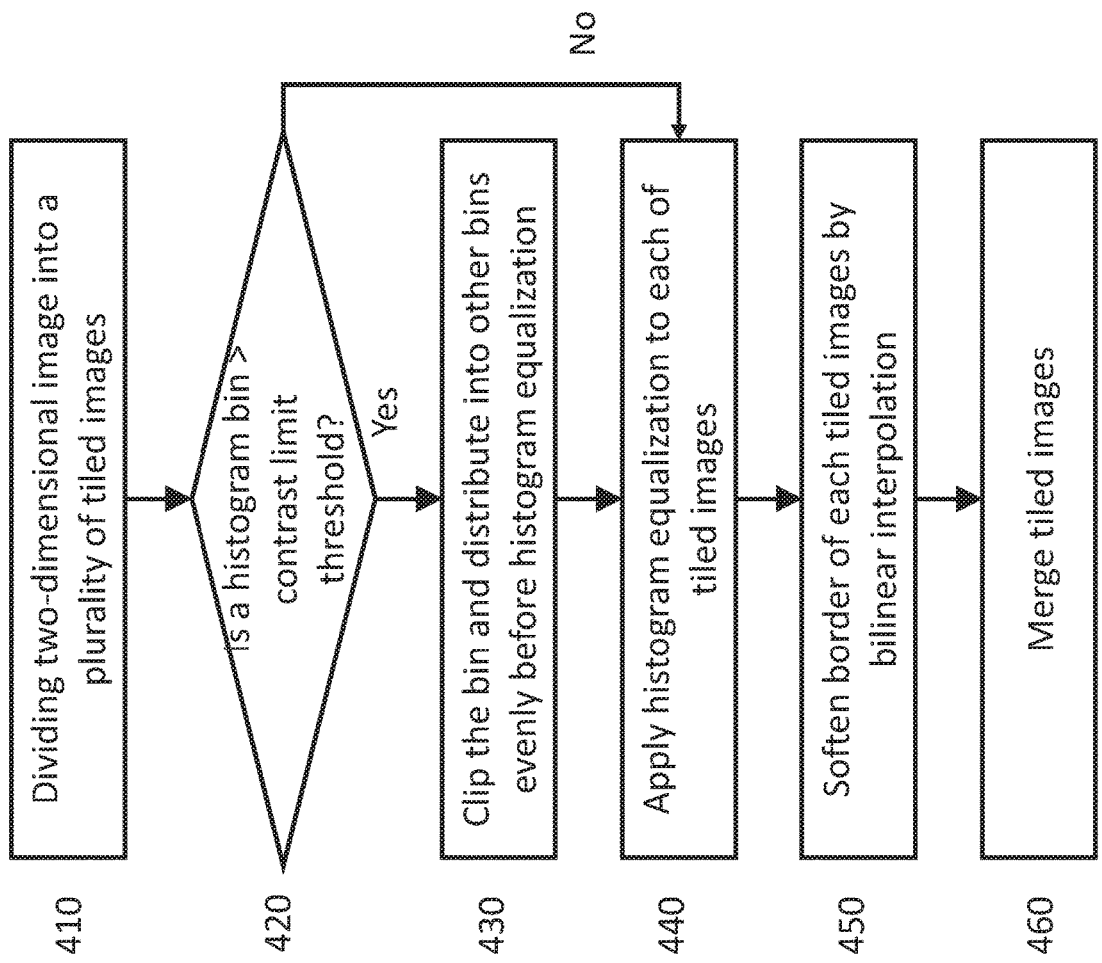
FIG. 4 is a flowchart of a process for applying adaptive histogram equalization to enhance the contrast of a 2D color image according to the concepts described herein.

Referring now to FIG. 4, a flowchart 400 for applying adaptive histogram equalization to enhance the contrast of a 2D color image is presented according to the concepts described herein. In processing block 410, a color image is divided into a plurality of tiled image having a smaller size than the dimension of the image. Adaptive histogram equalization may enhance the signal component of a color image, but it may also amplify the noise in the image. To address this problem, contrast limitation is introduced. In processing block 420, the system may check if there is a histogram bin that is greater than a predetermined contrast limit threshold β. If a bin has a greater value than the contrast limit threshold β, the corresponding pixels in the bin will be clipped and distributed evenly into other bins before histogram equalization (processing block 430). Then, in processing block 440, each tiled image may be histogram equalized using the standard histogram equalization method described above. In processing block 450, the system (e.g. via contrast enhancement unit 652) may apply bilinear interpolation to each tiled image to soften their borders to smooth the final product of the adaptive histogram equalization. In processing block 460, the tiled images may be merged into a color image. In some embodiments, the user may configure the threshold value β.

Figure 5:
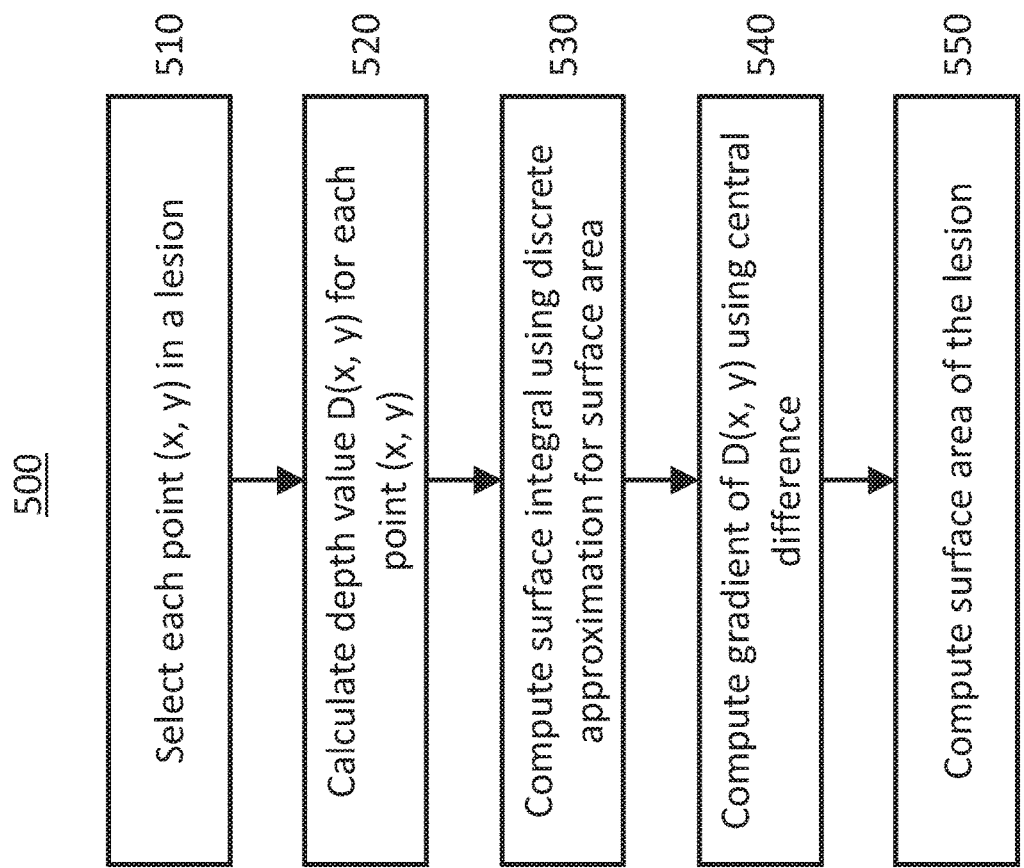
FIG. 5 is a flowchart of a process for calculating a three-dimensional (3D) surface area of a lesion according to the concepts described herein.

Referring now to FIG. 5, a flowchart for calculating a 3D surface area of a lesion is presented according to the concepts described herein. In this process, depth of points in a lesion (or distances to the points) is considered when calculating the 3D surface area.

Significantly, prior art techniques for calculating area is to simply count the number of pixels in a lesion. However, when processing an image of a curved surface, a significant problem with this approach is that only the projected surface area is captured. Accordingly, area calculation does not provide a correct measurement.

In contrast, the system and techniques described herein consider the depths of each point or pixels which allows the system to measure the area of lesions on a curved surface more accurately than prior art techniques.

A process to project surface area from curved surface to allow for accurate determination of a 3D surface area begins with processing block 510 in which each point (x, y) of a lesion S is selected.

Processing then proceeds to processing block 520 in which a corresponding depth value of the point (x, y) may be calculated. This value is obtained from the depth image 128 captured by the camera 110 in FIG. 1. The system may store a paired value P=(x, y, z)=(x, y, D(x, y)) where D(x, y) is a depth value of the point (x, y). In processing block 530, surface integral of the lesion S is calculated according the following formula:

$$A = \int\int_T \left\| \left(1, 0, \frac{\partial D}{\partial x}\right) \times \left(0, 1, \frac{\partial D}{\partial y}\right) \right\| dxdy = \int\int_T 1 dxdy = T$$

The surface integral takes a continuous depth function, but data from a hardware may be discrete. In this situation, the system may calculate surface area using a discrete approximation. For example, when the hardware has a field of view $F_x \times F_y$ degrees with a resolution of $R_x \times R_y$ pixels. If the camera is ideal without distortion, then each pixel corresponds to a field of view of $\theta_x \times \theta_y$ degrees where $\theta_x = F_x/R_x$ and $\theta_y = F_y/R_y$. For a projected surface ΔS with width Δx and height Δy at distance D may be captured in one single pixel. In this case, if both $\theta_x$ and $\theta_y$ are small, then the values may be calculated by trigonometry as, $\Delta x = D\theta_x$ and $\Delta y = D\theta_y$. Thus, ΔS is calculated as $\Delta x \Delta y = D^2 \theta_x \theta_y$.

Since the surface is not necessarily flat, the gradient of the depth needs to be incorporated in order to give a better approximation. In processing block 540, the gradient of depth at pixel (x, y) may be approximated using the central deference theorem. In the central difference theorem, if a function is evaluated at values that lie to the left and right of x, then the best two-point formula will involve values on the x-coordinate that are chosen symmetrically on both sides of x.

Figure 8:
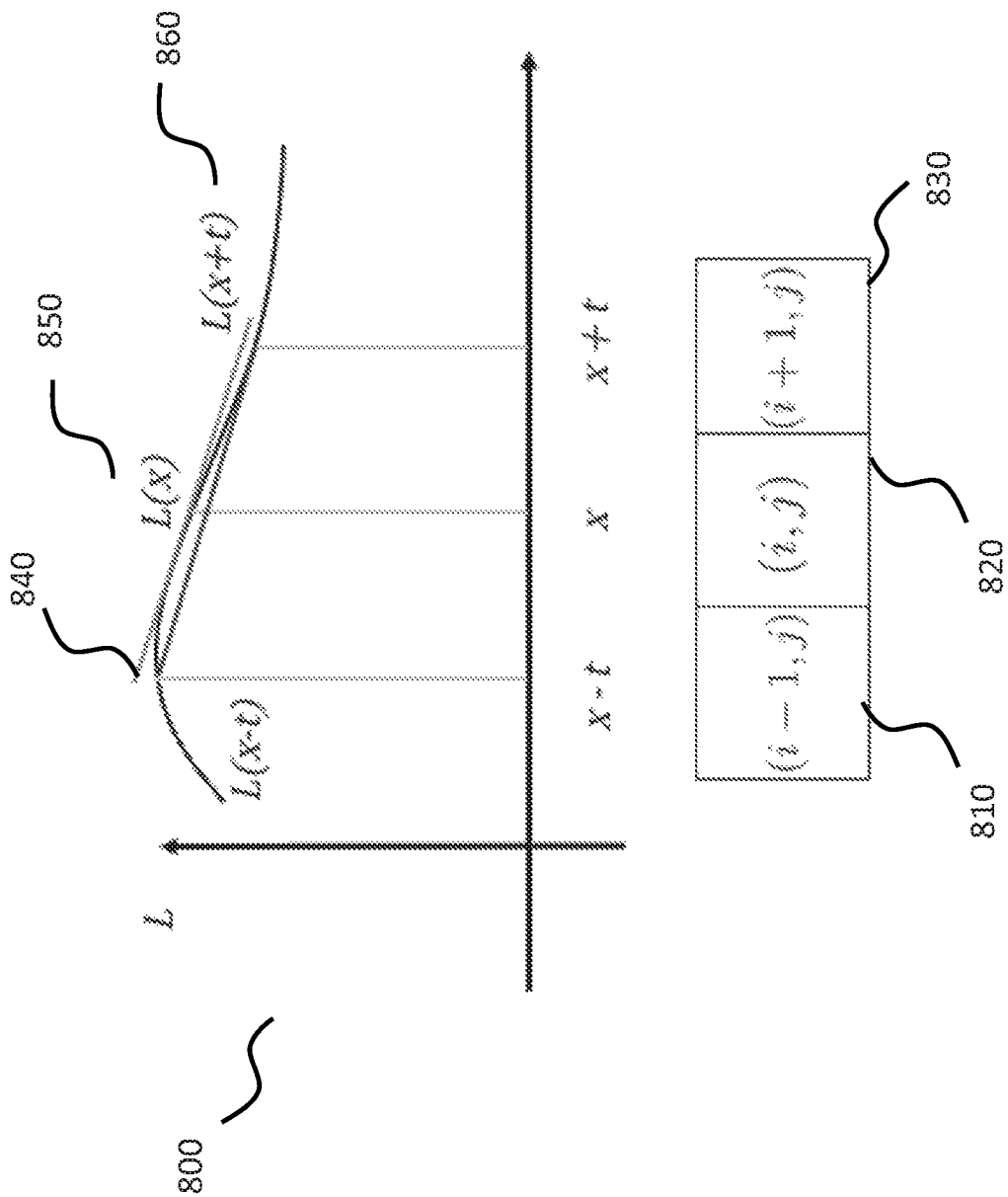
FIG. 8 is an illustrative plot of distance (X) vs. depth (L) showing how a central difference algorithm is used to calculate a gradient of a depth value according to the concepts described herein.

Now referring briefly FIG. 8, an illustrative plot 800 of distance (X) vs. depth (L) showing how a central difference algorithm is used to calculate a gradient of a depth value is presented according to the concepts described herein. In this illustrative example, three horizontally aligned pixels (i−1, j) 810, (i, j) 820 and (i+1, j) 830 that correspond to physical locations x−t, x and x+t are considered. These locations have distances or depths L(x−t) 840. L(x) 850 and L(x+t) 860 respectively, where L(x)=D(i, j). When a single pixel has a horizontal field angle of $\theta_x$, t may be $D\theta_x$. Then, at location x or pixel (i, j), the horizontal gradient approximation is given by the following formula:

$$\frac{\partial L(x)}{\partial x} \approx \frac{L(x+t) - L(x-t)}{2t} = \frac{D(i+1, j) - D(i-1, j)}{2D(i, j)\theta_x} \equiv D_x(i, j)$$

Using the same argument, the vertical gradient approximation may calculated as:

$$\frac{\partial L(y)}{\partial y} \approx \frac{L(y+t) - L(y-t)}{2t} = \frac{D(i, j+1) - D(i, j-1)}{2D(i, j)\theta_y} \equiv D_y(i, j)$$

Referring back to FIG. 5, in processing block 550, the surface area of the lesion may be calculated as the sum of the area of each pixel considering the depth value of each of the pixel. The calculation may be represented by the following formula:

$$\text{Lesion area} \cong \sum_{(i,j) \in \text{Lesion}} D(i, j)^2 \sqrt{D_x(i, j)^2 + D_y(i, j)^2 + 1} \theta_x \theta_y$$

Figure 6:
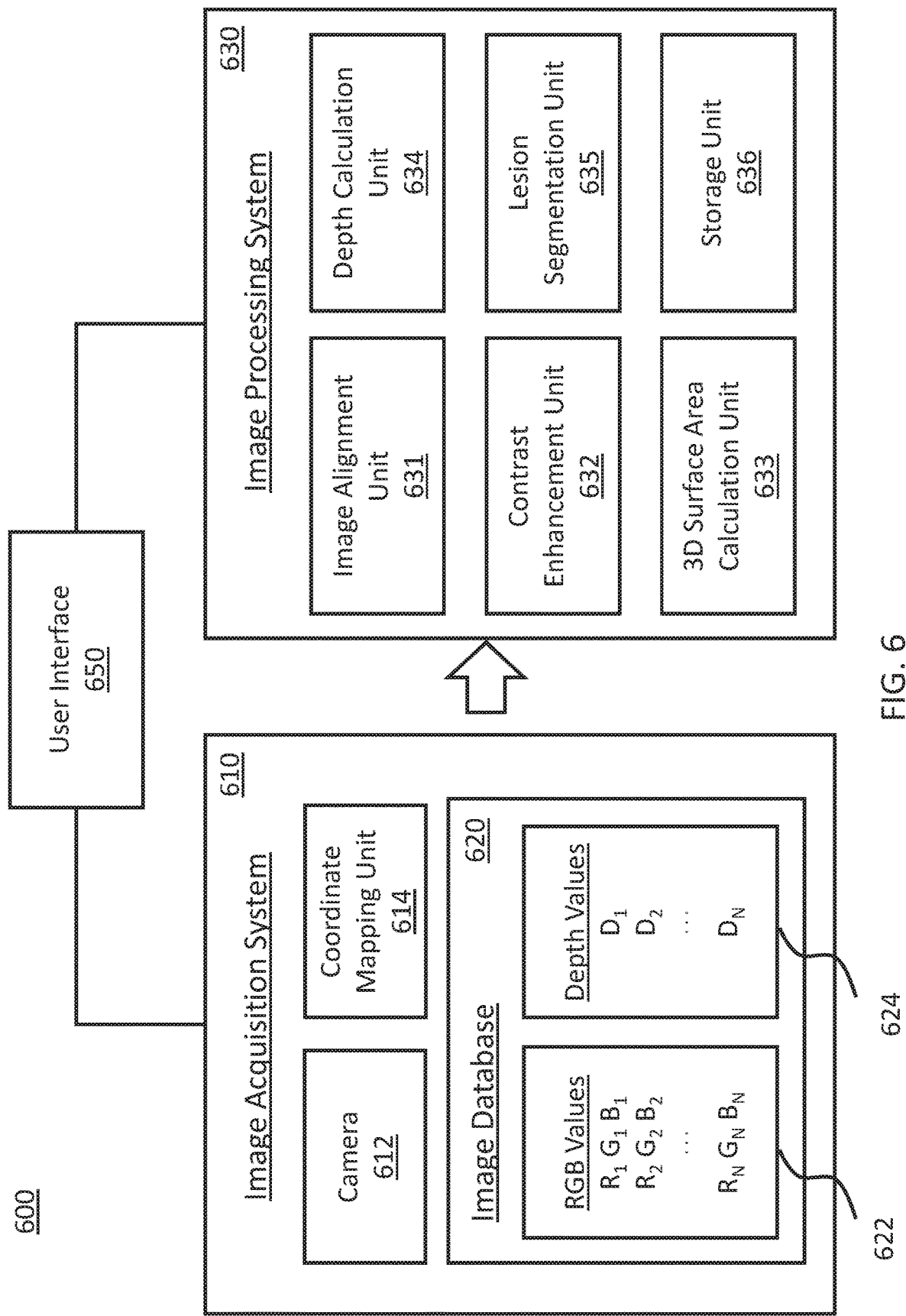
FIG. 6 is a block diagram of an illustrative automated surface area assessment system according to the concepts described herein.

Referring now to FIG. 6, an illustrative structure diagram of an automated surface area assessment system 600 is presented according to the concepts described herein. In an embodiment, the automated surface area assessment system 600 may comprise of two sub-systems. The first sub-system is an image acquisition system 610. The image acquisition system 620 may include a camera or other image acquisition device 612, a coordinate mapping unit 614, and an image database 620. The second sub-system is an image processing system 630. The image processing system 630 may include an image alignment unit 631, a contrast enhancement unit 632, a 3D surface area calculation unit 633, a depth calculation unit 634, a lesion segmentation unit 635, and a storage unit 636. The system 600 also may have a user interface 650. However, as can be appreciated by those of ordinary skill in the pertinent art, the structures of the sub-systems and their elements may have various combinations. For example, in embodiments, it may be desirable or necessary for either or both of the image alignment unit contrast enhancement unit and to be provided as part of the image acquisition system.

Also, two sub-systems, except the camera 612, may be part of one system, such as a computer, server, or a laptop. Alternately, the automated surface area assessment system 600 may be distributed to more than two sub-systems.

The camera 612 may capture a 2D color image and a depth image of a target 3D surface area. In an illustrative embodiment, the camera may a Microsoft Kinect. Alternately, the camera may be a different camera that captures a 2D color image and a depth image of a surface area. Herein, the color image may be an RGB image that comprises a vector of three values stored in each pixel. Alternately, the color image may have a different format, such as a CMYK color image. The color image and the depth image may be stored in the image database 620. For example, RGB values 622 of the color image are stored as a set of vectors $(R_1, G_1, B_1), (R_2, G_2, B_2) \ldots (R_N, G_N, B_N)$. Similarly, depth values 624 of the depth image are stored as a set of values $D_1, D_2, \ldots D_N$. The image database 620 may be a generic-purpose database or a database that is specifically designed for storing image data. The image files may be stored in a native RGB format, as illustrated in FIG. 6. Alternately, the system 600 may parse the image data into a different format for later use and store the parsed data. In some embodiments, the system may store both the original image files and parsed data files. The coordinate mapping unit 614 may map each color pixel of the color image to corresponding depth pixel in the depth image in order to obtain depth information. In some embodiments, the camera 612 may embed a coordinate mapping unit 614 to produce a color image, a depth image, and mapping data. Alternately, the coordinate mapping 614 may be part of the image processing system 630.

The image processing system 630 may perform preparation tasks, before calculating the area of lesions in the surface area, such as image alignment, or contrast enhancement. The image alignment unit 631 may align the 2D color image with the depth image. The contrast enhancement unit 632 may enhance the contrast of the color image using the process described in process 300 and 400 in FIGS. 3-4. The depth calculation unit 634 may calculate depth value from the depth image for each point in the color image. These values may be obtained from the depth image. The lesion segmentation unit 635 segments lesions of the 3D surface area. The lesion segmentation unit 635 may apply a grapcut algorithm or a watershed algorithm to segment the lesions. The 3D surface area calculation unit 633 may calculate the area of lesions on a 3D surface area using the process 500 described in FIG. 5. The storage unit 636 may store any data files or intermediate data that are required to perform an automated surface area assessment. The user interface 650 may interact with a user (not shown). The user may configure one or more algorithms to be applied for contrast enhancement of the color image, or a type of segmentation method. The user interface 650 may be used to determine a lesion to segment as part of the segmentation processing.

Figure 7:
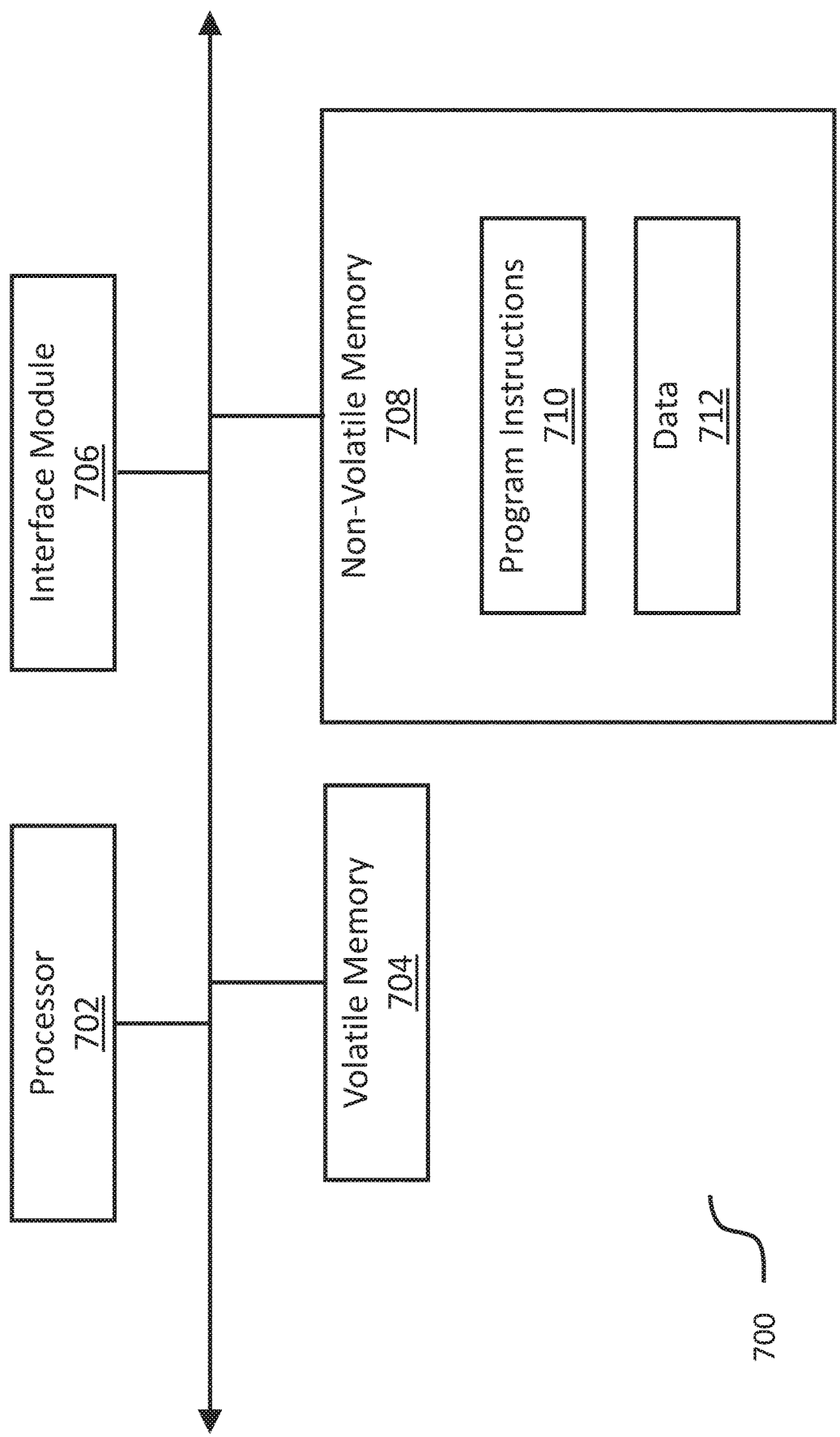
FIG. 7 is a block diagram of an illustrative implementation of an automated surface area assessment system described in FIG. 6 according to the concepts described herein.

Referring now to FIG. 7, an exemplary implementation of a processing device 700 is described according to the concepts described herein. The processing device 700 includes a processor 702, a volatile memory 704, a non-volatile memory 706 (e.g., hard disk) and the interface module 708 (e.g., a user interface, USB interface and so forth). The non-volatile memory 706 stores computer instructions 712, an operating system 716 and data 718. In one example, the computer instructions 712 are executed by the processor 702 out of volatile memory 704 to perform all or part of the processes described herein (e.g., processes 200, 300, 400, or 500).

The processes described herein (e.g., process 200, 300, 400, and 500) is not limited to use with the hardware and software of FIGS. 1, 6 and 7; they may find applicability in any computing or processing environment and with any type of machine or set of machines that is capable of running a computer program. The processes described herein may be implemented in hardware, software, or a combination of the two. The processes described herein may be implemented in computer programs executed on programmable computers/machines that each includes a processor, a non-transitory machine-readable medium or another article of manufacture that is readable by the processor (including volatile and non-volatile memory and/or storage elements), at least one input device, and one or more output devices. Program code may be applied to data entered using an input device to perform any of the processes described herein and to generate output information.

The system may be implemented, at least in part, via a computer program product, (e.g., in a non-transitory machine-readable storage medium such as, for example, a non-transitory computer-readable medium), for execution by, or to control the operation of, data processing apparatus (e.g., a programmable processor, a computer, or multiple computers). Each such program may be implemented in a high level procedural or object-oriented programming language to work with the rest of the computer-based system. However, the programs may be implemented in assembly, machine language, or Hardware Description Language. The language may be a compiled or an interpreted language and it may be deployed in any form, including as a stand-alone program or as a module, component, subroutine, or another unit suitable for use in a computing environment. A computer program may be deployed to be executed on one computer or multiple computers at one site or distributed across multiple sites and interconnected by a communication network. A computer program may be stored on a non-transitory machine-readable medium that is readable by a general or special purpose programmable computer for configuring and operating the computer when the non-transitory machine-readable medium is read by the computer to perform the processes described herein. For example, the processes described herein may also be implemented as a non-transitory machine-readable storage medium, configured with a computer program, where upon execution, instructions in the computer program cause the computer to operate in accordance with the processes. A non-transitory machine-readable medium may include but is not limited to a hard drive, compact disc, flash memory, non-volatile memory, volatile memory, magnetic diskette and so forth but does not include a transitory signal per se.

By using the concepts described herein, the system 600 may provide an absolute measurement of the surface area of lesions absolute measurement of the lesions (i.e. a measurement corresponding to a specific area measurement of a lesion—e.g. in say squared mm), taking curvature of the lesion surface into account. The system 600 also is contact-free. This eliminates the possibility of contamination and discomfort caused by manual tracing. In addition, the system may operate without any calibration or professional training. The system 600 may not need any special hardware for image capture, or specialized lighting and works with off the shelf components. The method to assess surface area has no dependency on the hardware used to capture the color and depth image, as long as the mapping from the color image to the depth image is known.

The anticipated applications of the concepts described herein may be to determine the burden of disease and response to treatment for patient care and clinical trial applications. In some embodiments, vitiligo, eczema, psoriasis, and chronic wounds may be immediate areas for assessing surface area by the system 600. In addition, determination of BSA of adverse dermatologic side effects would allow for granular, objective grading of adverse events or determination of BSA involvement in burns or wounds.

Having described preferred embodiments, which serve to illustrate various concepts, structures and techniques, which are the subject of this patent, it will now become apparent that other embodiments incorporating these concepts, structures and techniques may be used. Accordingly, it is submitted that the scope of the patent should not be limited to the described embodiments but rather should be limited only by the spirit and scope of the following claims.

Accordingly, other embodiments are within the scope of the following claims.

What is claimed is:

1. A method for assessing a three-dimensional (3D) surface area having one or more lesions, the method comprising:
capturing a two-dimensional (2D) color image and a depth image of the 3D surface area, the depth image being an image in which each pixel has associated therewith a distance to a corresponding point on the surface being imaged;
enhancing contrast of the 2D color image;
segmenting the one or more lesions of the 2D color image into one or more segmented lesions; and
calculating a 3D surface area of the one or more segmented lesions using enhanced contrast information from the 2D color image and distance information from the depth image.

2. The method of claim 1 further comprising:
calibrating at least one parameter for processing the depth image.

3. The method of claim 1 further comprising:
mapping pixels of the 2D color image to depth pixel of the depth image.

4. The method of claim 1, the enhancing contrast of the 2D color image further comprising:
applying gamma correction to each of color channels of the 2D color image.

5. The method of claim 1, the enhancing contrast of the 2D color image further comprising:
applying histogram equalization to the 2D color image.

6. The method of claim 1, the enhancing contrast of the 2D color image further comprising:
dividing the 2D color image into a plurality of tiled images;
applying the histogram equalization method to each of the tiled images; and
combining the plurality of images into a combined two-image.

7. The method of claim 6, the enhancing contrast of the 2D color image further comprising:
softening borders of each of the tiled images by applying the bilinear interpolation method.

8. The method of claim 1, further comprising:
converting a first color space of the 2D color image into a second color space;
adjusting a lightness channel of the 2D color image; and
converting the second color space of the 2D color image to the first color space.

9. The method of claim 1, the segmenting the surface area further comprising:

segmenting the one or more lesions of the 2D color image into one or more segmented lesions using the watershed transformation.

10. The method of claim 1, the calculating 3D area of the one or more lesions further comprising:
calculating depth values for each pixel of the depth image; and
calculating the 3D area of one or more lesions considering the depth values.

11. The method of claim 10, the calculating 3D area of the one or more lesions further comprising:
calculating the 3D area of one or more lesions considering the gradient of the depth values.

12. The method of claim 11, further comprising:
approximating the gradient of the depth values using a central difference of horizontally aligned pixels and vertically aligned pixels in the depth image.

13. The method of claim 1, wherein calculating the 3D surface area of the one or more segmented lesions further comprises:
calculating the 3D surface area of the one or more segmented lesions using the following formulas:

$$\text{Lesion area} \cong \sum_{(i,j)\in Lesion} D(i,j)^2 \sqrt{D_x(i,j)^2 + D_y(i,j)^2 + 1\theta_x\theta_y}$$

$$D_x(i,j) = \frac{D(i+1,j) - D(i-1,j)}{2D(i,j)\theta_x}$$

$$D_y(i,j) = \frac{D(i,j+1) - D(i,j-1)}{2D(i,j)\theta_y}$$

where (i, j) are pixel coordinates, D(i, j) is the depth of pixel (i, j), and the camera has a field of view Fx×Fy degrees with a resolution of Rx×Ry pixels and each image pixel corresponds to a field of view of θx×θy degrees where θx=Fx/Rx and θy=Fy/Ry.

14. The method of claim 1 further comprising:
measuring distance to each of pixels of the depth image by measuring the time of flight between the each of pixels and a camera capturing the depth image.

15. The method of claim 1, further comprising:
converting an RGB color space of the 2D color image into a Lab color space;
adjusting a lightness channel of the 2D color image; and
converting the Lab color space of the 2D color image to the RGB color space.

16. An apparatus for assessing a three-dimensional (3D) surface area having one or more lesions, the apparatus comprising:
a camera capturing a two-dimensional (2D) color image and a depth image of the 3D surface area, the depth image being an image in which each pixel has associated therewith a distance to a corresponding point on the surface being imaged; and
a processor and a memory, wherein the processor is configured to:
enhance contrast of the 2D color image;
segment the one or more lesions of the 2D color image into one or more segmented lesions; and
calculate a 3D surface area of the one or more segmented lesions using enhanced contrast information from the 2D color image and distance information from the depth image.

17. The apparatus of claim 16, wherein the camera measures distance to each of pixels of the depth image by measuring the time of flight between the each of pixels and the camera.

18. The apparatus of claim 16, further comprising a user interface with which a user enhances the contrast of the 2D color image.

19. The apparatus of claim 18, wherein the user selects a type of histogram equalization to enhance the contrast of the 2D color image via the user interface.

* * * * *